US00PP36424P2

(12) United States Plant Patent
Dirr et al.

(10) Patent No.: US PP36,424 P2
(45) Date of Patent: Feb. 4, 2025

(54) ***LOROPETALUM* PLANT NAMED 'LRD-51-22'**

(50) Latin Name: ***Loropetalum chinense* var. *rubrum***
Varietal Denomination: LRD-51-22

(71) Applicant: Premier Introductions Inc., Watkinsville, GA (US)

(72) Inventors: Michael Dirr, Bogart, GA (US); Jeff Beasley, Lavonia, GA (US); Mark Griffin, Watkinsville, GA (US)

(73) Assignee: Premier Introductions Inc., Watkinsville, GA (US)

( * ) Notice: Subject to any disclaimer, the term of this patent is extended or adjusted under 35 U.S.C. 154(b) by 0 days.

(21) Appl. No.: 18/762,141

(22) Filed: Jul. 2, 2024

(51) Int. Cl.
*A01H 5/00* (2018.01)
*A01H 6/00* (2018.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — Cassandra Bright

(57) ABSTRACT

A new and distinct cultivar of *Loropetalum chinense* var. *rubrum* plant named 'LRD-51-22', characterized by its compact, low-growing habit; lustrous dark black-purple foliage color that persists through summer and winter; dark pink flowers in spring; and improved cold hardiness compared to other compact purple-leaf cultivars. The new variety is a *Loropetalum*, typically for ornamental garden use.

2 Drawing Sheets

Genus and species of plant claimed: *Loropetalum chinense* var. *rubrum*.

Variety denomination: 'LRD-51-22'.

BACKGROUND OF THE INVENTION

The present invention relates to a new and distinct cultivar of *Loropetalum chinense* var. *rubrum*, a member of the Hamamelidaceae family, hereinafter referred to by its cultivar name 'LRD-51-22'. This cultivar is grown primarily as an ornamental for landscape use and for use as a potted plant.

The cultivar originated from an open-pollination of *Loropetalum chinense* var. *rubrum* 'GriffCRL', U.S. Plant Pat. No. 16,615, in Watkinsville, Georgia, in 2022, and was selected from the progeny by continued evaluation for growth habit, flower, and improved foliage characteristics. The cultivar 'LRD-51-22' originated and was discovered in a cultivated environment in an outdoor nursery in Watkinsville, Georgia.

'LRD-51-22' has been asexually reproduced by softwood cuttings since 2022 in Watkinsville, Georgia. The characteristics of the cultivar have been stable and reproduced true to type in successive vegetative generations.

SUMMARY OF THE INVENTION

'LRD-51-22' has not been observed under all possible environmental conditions. The phenotype may vary somewhat with changes in light, temperature, soil and rainfall without, however, any variance in genotype.

The following traits have been observed and represent the characteristics of the new cultivar. In combination, these characteristics distinguish 'LRD-51-22' from all other varieties in commerce known to the inventor:

1. Compact, low-growing habit.
2. Small leaves.

3. Lustrous dark black-purple foliage color that persists through summer and winter.
4. Dark pink flowers in spring.
5. Improved cold hardiness compared to other compact, purple-leaf cultivars.

PARENTAL COMPARISON

Plants of the new cultivar 'LRD-51-22' are comparable to the seed parent in most horticultural characteristics. However, the new variety 'LRD-51-22' differs in the following:

1. 'LRD-51-22' has a compact mounded, spreading growth habit, whereas the seed parent has an overall larger, rounded growth habit.
2. 'LRD-51-22' has dark black-purple foliage that persists through summer and winter, whereas 'GriffCRL' has duller red-purple foliage that will become greenish-purple in summer and winter.
3. 'LRD-51-22' has dark pink flowers (almost red), whereas 'GriffCRL' has light pink flowers.

COMMERCIAL COMPARISONS

Plants of the new cultivar 'LRD-51-22' can be compared to the commercial cultivar 'PIILC-I', U.S. Plant Pat. No. 25,534, in most horticultural characteristics. However, the new variety 'LRD-51-22' differs in the following:

1. 'LRD-51-22' has dark black-purple foliage, whereas 'PIILC-I' has rich reddish-purple foliage that is mounding.
2. 'LRD-51-22' has dark pink flowers, whereas 'PIILC-I' has bright pink flowers.

Plants of the new cultivar 'LRD-51-22' can be compared to the commercial cultivar 'PIILC-III', U.S. Plant Pat. No. 25,471, in most horticultural characteristics. However, the new variety 'LRD-51-22' differs in the following:

1. 'LRD-51-22' has foliage that is dark black-purple with a dark pink (close to red) flower. 'PIILC-III' has foliage that is dark purplish-grey and a moderate purplish-red flower.

BRIEF DESCRIPTION OF THE PHOTOGRAPHS

The accompanying illustrations show characteristics of the new cultivar in photographs as true to color as is reasonably possible to make in illustrations of this nature. Colors in the photographs may differ slightly from the color values cited in the detailed botanical description which accurately describe the colors of the new *Loropetalum*.

DETAILED BOTANICAL DESCRIPTION

Figure 1:
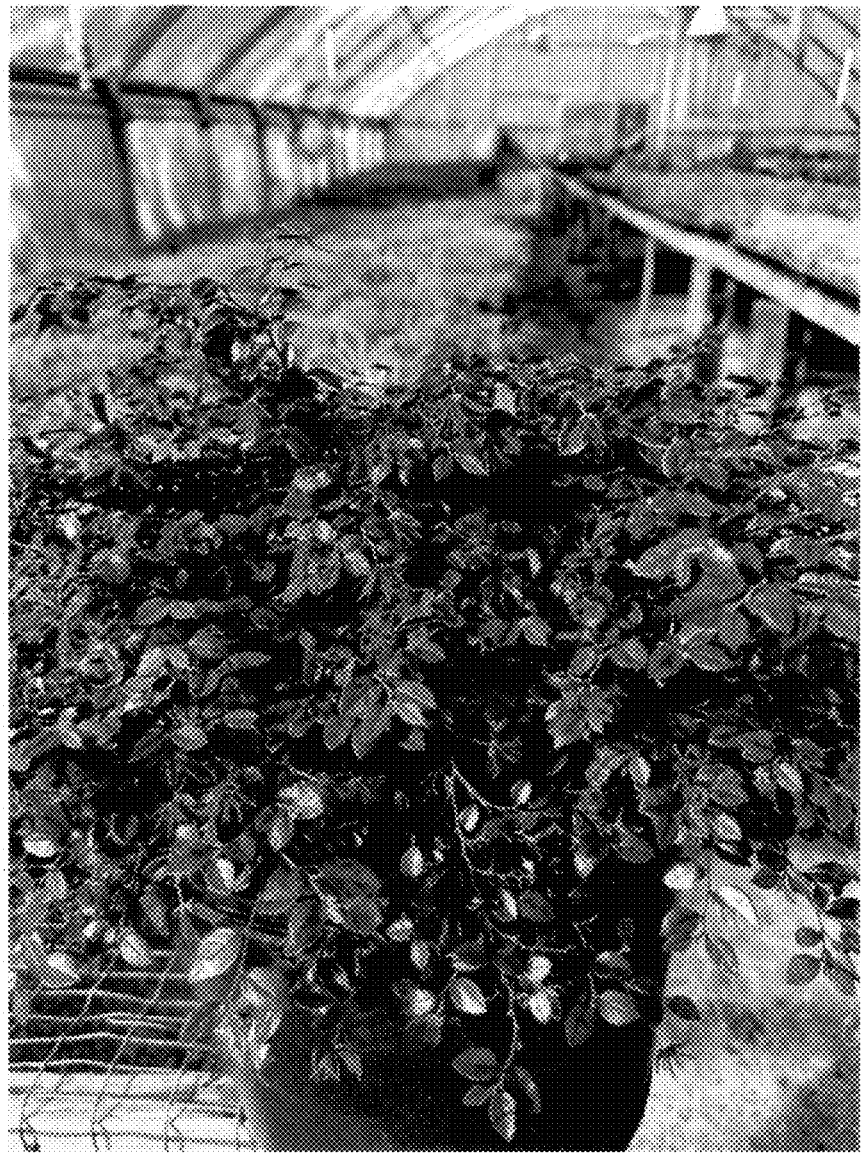
FIG. 1 illustrates the flower and foliage colors of a 'LRD-51-22' plant growing in a container.
Figure 2:
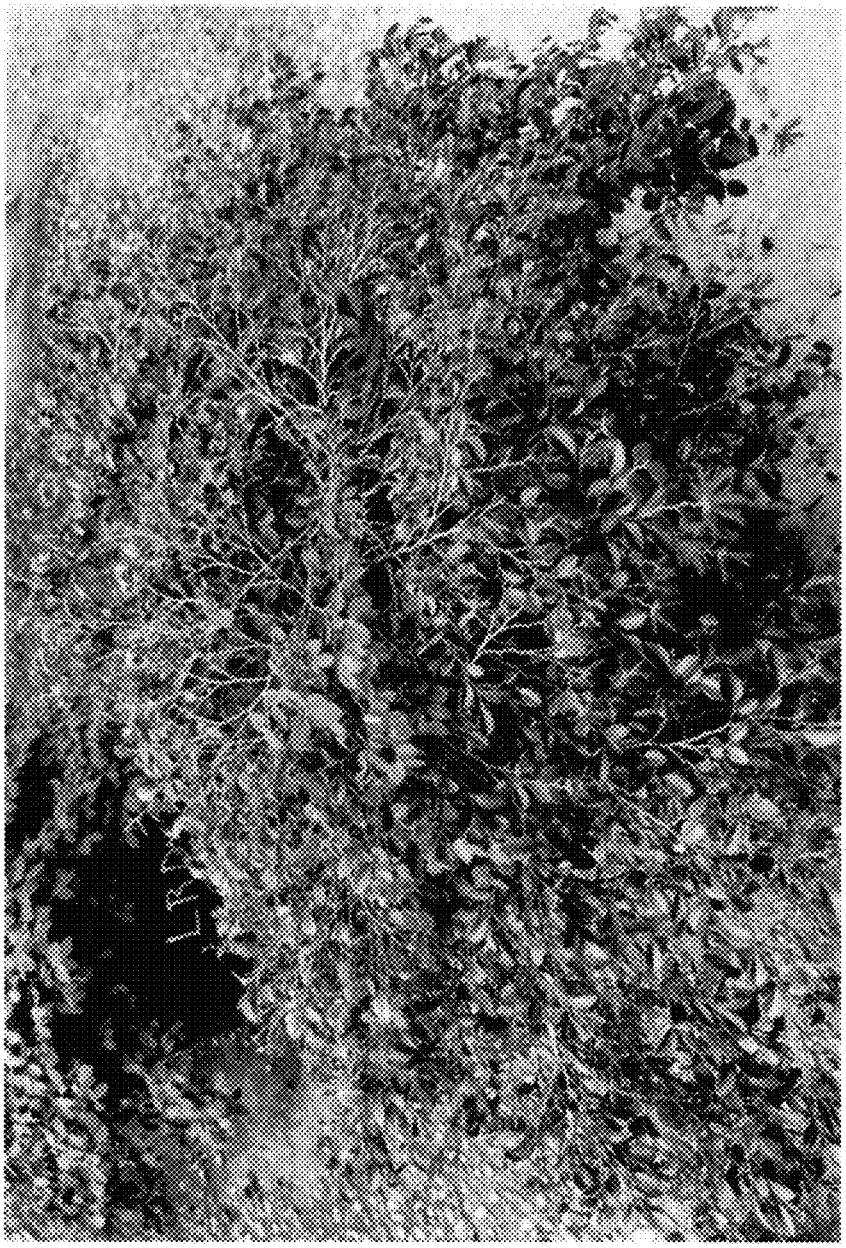
FIG. 2 illustrates the habit of 'LRD-51-22'.

In the following description, color references are made to The Royal Horticultural Society Colour Chart, 2015 Edition, except where general terms of ordinary dictionary significance are used. Plants for the description were grown in a container under outdoor conditions in Watkinsville, GA. Plants were about two years old when the description was recorded.

Botanical classification: *Loropetalum chinense* var. *rubrum* 'LRD-51-22'.

PROPAGATION

Type of propagation typically used: Vegetative terminal cuttings.

Time to initiate roots: About 35 days at 32° C. in summer.

Number of days to produce a rooted plant in summer: 110 days at 27° C.

Root description: Numerous, fine, fibrous and well-branched. Colored RHS Purple N77B.

PLANT

Type of plant: Flowering shrub.

Age of plant described: 2 years old.

Container size of the plant described: 11.35 liters.

Growth habit: Compact, mounded, spreading. Freely branching; pruning enhances lateral branch development.

Height: 10 cm.

Plant spread: 88 cm.

First year stems:

- *Length*.—About 13 cm.
- *Diameter*.—About 2 mm.
- *Shape*.—Round.
- *Color*.—RHS Brown 201A.
- *Pubescence*.—Heavily stellate.

Second year stems:

- *Length*.—30 to 35 cm.
- *Diameter*.—3 mm or more.
- *Shape*.—Round.
- *Color*.—RHS Brown N199A.
- *Pubescence*.—None.

Trunk/main stem diameter: About 2 cm at the soil line.

Trunk/main stem color: RHS Brown N199A.

- *Strength*.—Flexible when young, more easily broken when mature.
- *Bark*.—Exfoliates in flakes beginning on second year stems.

Internode length: About 5 mm.

Vegetative buds:

- *Arrangement*.—Alternate, imbricate.
- *Length*.—About 2 mm.
- *Width*.—About 1 mm.
- *Color*.—RHS Purple N77A.
- *Pubescence*.—Stellate.

FOLIAGE

Leaf:

- *Arrangement*.—Alternate, simple.
- *Average length*.—1 cm.
- *Average width*.—8 mm.
- *Shape of blade*.—Ovate, rounded.
- *Apex*.—Pointed.
- *Base*.—Oblique.
- *Margin*.—Finely-toothed.
- *Texture of top surface*.—Stellate or sandpaper-like pubescence.
- *Texture of bottom surface*.—Stellate or sandpaper-like pubescence.
- *Color*.—Young foliage upper side: RHS Purple N77A. Young foliage under side: RHS Purple 71A. Fully expanded foliage upper side: RHS Red 186A. Fully expanded foliage under side: RHS Purple N77A.
- *Venation*.—Type: Pinnate. Color, young foliage, upper side: RHS Purple N77A. Color, young foliage, under side: RHS Purple N79B. Color, mature foliage upper side: RHS Red 187A. Color, mature foliage under side: RHS Red 187B.
- *Petiole*.—Length: About 3.5 mm. Diameter: About 1 mm. Color: RHS Purple N77A. Pubescence: Stellate.

FLOWER

Natural flowering season: Flowers are produced in April in Watkinsville, GA, and sporadically until frost. An inflorescence is showy for about 2 weeks, and individual flowers last about 2 to 3 days.

Inflorescence and flower type and habit: Umbel produced terminally and from leaf axils.

Inflorescence shape: 4 to 5 strap-like petals forming a loose funnel.

Inflorescence diameter: 1 to 2 cm.

Inflorescence depth: 8 mm.

Quantity of florets per inflorescence: 4 to 8.

Persistence: Self-Cleaning.

Fragrance: None.

Flower buds:

- *Arrangement*.—4 to 8 flowers from globose heads on branchlet terminals.
- *Shape*.—Orbicular.
- *Length*.—About 2 mm.
- *Diameter*.—About 2 mm.
- *Color*.—RHS Purple 77B.

Petals:

- *Quantity per flower*.—4.
- *Shape*.—Strap-shaped.
- *Margin*.—Entire.
- *Texture*.—Smooth.
- *Length*.—About 1.1 cm.
- *Width*.—About 2 mm.
- *Apex*.—Acuminate.
- *Base*.—Obtuse.

*Color*.—Upper surface: RHS Red 60B. Lower surface: RHS Red 60B.

Sepals:

*Quantity per flower*.—4.
*Texture*.—Pubescent.
*Arrangement*.—Opposite.
*Shape*.—Ovate.
*Length*.—2 mm.
*Width*.—2 mm.
*Apex*.—Acute to obtuse turning outward.
*Base*.—Fused onto calyx cup.
*Margin*.—Entire.
*Color*.—Upper side: RHS Purple-Red 64A. Under side: RHS Red 59A.

Peduncle:

*Length*.—About 6 mm.
*Diameter*.—About 1 mm.
*Texture*.—Stellate pubescence.
*Color*.—RHS Purple 71A.

Calyx:

*Length*.—About 3.5 mm.
*Diameter*.—About 2 mm.
*Color*.—RHS Purple 71A, both surfaces.
*Pubescence*.—Stellate.

REPRODUCTIVE ORGANS

Stamens:

*Number*.—4 or 5.
*Length*.—1.5 mm.
*Width*.—0.3 mm.
*Color*.—RHS Purple N77A.
*Pollen*.—Amount: Scant. Color: RHS Yellow-Green 156A.

Pistil:

*Number*.—1 or 2 inferior pistils per flower.
*Length*.—Approximately 2 mm.
*Color*.—RHS Purple 71A.
*Style*.—Length: 1 mm. Color: RHS Purple 71A.
*Stigma*.—Shape: Rounded. Color: RHS Purple 71A. Ovary: Length: 1 mm. Width: 1 mm. Color: RHS Purple N80B.

OTHER CHARACTERISTICS

Temperature tolerance: USDA Plant Hardiness Zone Map (2012): Zone 7 to 9.

Fruits and seeds: Not observed to date.

Disease/pest resistance: Plants of the claimed *Loropetalum* cultivar grown in the garden have not been noted to be susceptible or resistant to pathogens and pests common to *Loropetalum*.

What is claimed is:

1. A new and distinct *Loropetalum* plant named 'LRD-51-22', substantially as illustrated and described herein.

* * * * *